United States Patent [19]
Petrow

[11] Patent Number: 5,661,141
[45] Date of Patent: Aug. 26, 1997

[54] 19-OXYGENATED STEROIDS AS THERAPEUTIC AGENTS

[76] Inventor: Vladimir Petrow, 1905 Jones Ferry Rd., Chapel Hill, N.C. 27516

[21] Appl. No.: 409,832

[22] Filed: Mar. 27, 1995

[51] Int. Cl.$^6$ .................................................. A61K 31/56
[52] U.S. Cl. ........................ 514/177; 514/178; 514/181; 514/182
[58] Field of Search ................................. 514/177, 178, 514/181, 182

[56] References Cited

U.S. PATENT DOCUMENTS

| | | |
|---|---|---|
| 2,661,357 | 12/1953 | Huffman . |
| 3,067,198 | 12/1962 | Wettstein et al. . |
| 3,077,482 | 2/1963 | Wettstein et al. . |
| 3,077,486 | 2/1963 | Huffman . |
| 3,729,560 | 4/1973 | Hagerman . |
| 3,729,568 | 4/1973 | Kligman ................... 424/318 |
| 4,013,762 | 3/1977 | Benson et al. . |
| 4,022,769 | 5/1977 | Grunwell et al. . |
| 4,048,159 | 9/1977 | de Ruggieri et al. . |
| 4,054,651 | 10/1977 | Benson et al. . |
| 4,055,641 | 10/1977 | Benson et al. . |
| 4,071,624 | 1/1978 | Grunwell et al. . |
| 4,071,625 | 1/1978 | Grunwell et al. . |
| 4,078,060 | 3/1978 | Benson et al. . |
| 4,078,061 | 3/1978 | Benson et al. . |
| 4,087,524 | 5/1978 | Grunwell et al. . |
| 4,088,760 | 5/1978 | Benson et al. . |
| 4,096,254 | 6/1978 | Benson et al. . |
| 4,126,693 | 11/1978 | Gander et al. ................. 424/282 |
| 4,139,617 | 2/1979 | Grunwell et al. . |
| 4,239,681 | 12/1980 | Grunwell et al. . |
| 4,317,818 | 3/1982 | Benson et al. . |
| 4,396,615 | 8/1983 | Petrow et al. . |
| 4,499,021 | 2/1985 | Varma . |
| 4,512,986 | 4/1985 | Reel et al. . |
| 4,891,367 | 1/1990 | Angelastro et al. . |
| 4,966,897 | 10/1990 | Angelastro et al. . |
| 5,108,995 | 4/1992 | Casper . |
| 5,124,313 | 6/1992 | Schaeffer et al. . |
| 5,278,310 | 1/1994 | Raspanti . |
| 5,494,905 | 2/1996 | Hesse et al. . |

FOREIGN PATENT DOCUMENTS 976543 10/1975 Canada .

OTHER PUBLICATIONS

M.N. Mueller and A. Kappas; *Estrogen Parmacology. II. Suppression of Experimental Immune Polyarthritis (29715), Estrogens Biol. Animal* pp. 845–847 (1964).

R.E. Counsell et al; *Chemical and Biological Properties of Some 17-Substituted Estradiol Derivatives*, Journal of Medicinal Chemistry 9, pp. 689–692 (1966).

A.S. Spangler et al; *Enhancement of the Anti-inflammatory Action of Hydrocortisone by Estrogen*, Estrogens 29, pp. 650–655 (1969).

M.Dyson and J. Joseph; *The Effects of Female Sex Hormones on Tissue Regeneration in the Rabbit's Ear*, J. Endocr. 51, pp. 685–697 (1971).

R. Müller; *Estrogens as additives in shampoos*, Hautarzt 24, pp. 130–131 (1973).

M.N. Goodman and R.L.Hazelwood; *Short-Term Effects of Oestradiol Benzoate in Normal, Hypophysectomized and Alloxan-Diabetic Male Rats*, J. Endocr 62, pp. 439–449 (1974).

H. Hosoda and J. Fishman; *Unusually Facile Aromatization of 2β-Hydroxy-19-oxo-4-androstene-3,17-dione to Estrone. Implications in Estrogen Biosynthesis*, Journal of American Chemical Society 96, pp. 7325–7329 (1974).

J.O. Johnston et al; *Behavioral Effects of 19-Hydroxytestosterone; Sexual Behavior: Pharmacology and Biochemistry* pp. 227–240 (1975).

C.E. Orfanos and H. Wüstner; *Penetration and Side Effects of Local Application of Estrogen in Androgenetic Alopecia*; Hautarzt 26 pp. 367–369 (1975).

H. U. Schweikert et al; *Aromatization of Androstenedione by Isolated Human Hairs*, JCE & M 40, No.3, pp. 413–417 (1975).

L.A. Rigg et al; *Efficacy of Intravaginal and Intranasal Administration of Micromized Estradiol-17β*; Journal of Clinical Endocrinology & Metabolism, 46 No. 6., pp. 1261–1264 (1977).

C.H. Phoenix; *Induction of Sexual Behavior in Ovariectomized Rhesus Females with 19-Hydroxytestosterone*; Hormones and Behavior 8, pp. 356–362 (1977).

R.F. Parrott; *Courtship and Copulation in Prepubertally Castrated Male Sheep (Wethers) Treated with 17β-Estradiol, Aromatizable Androgens, or Dihydrotestosterone*; Hormones and Behavior 11 pp. 20–27 (1978).

(List continued on next page.)

Primary Examiner—Kimberly J. Prior
Attorney, Agent, or Firm—Bell, Seltzer, Park & Gibson

[57] ABSTRACT

The present invention provides compounds and methods of inducing a variety of therapeutic responses in a subject in need of such treatment. The method includes administering a compound of Formula (I)

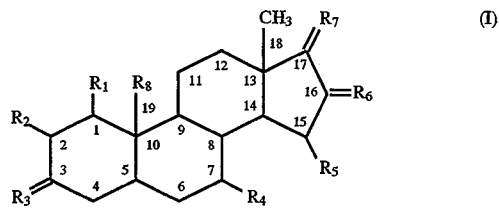

wherein $R_1$–$R_7$ are as defined in the specification;

and wherein said compound of Formula (I) is ethylenically unsaturated at a set of locations selected from the group consisting of (a) between $C_4$ and $C_5$; (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and between $C_7$ and $C_8$.

The compounds of Formula (I) are administered in an amount effective to induce the desired therapeutic response.

9 Claims, No Drawings

OTHER PUBLICATIONS

T.A. Marks and V. Petrow; *Effect of the Preestrogen 4-Androstene-3,17-dion-19-al on the Dunning R3327 Prostatic Adenocarcinoma;* Cancer Research 43, pp. 3687,3690 (1983).

N. S. Latman: *Relation of Menstrual Cycle Phase to Symptoms of Rheumatoid Arthritis;* The American Journal of Medicine 74, pp. 957–960 (1983).

J.M. Gottswinter et al; *Gynecomastia caused by estrogen containing hair lotion;* J. Endocrinol. Invest 7 pp. 383–386 (1984).

L.J. Carrigton and C.J. Bailey; *Effects of Natural and Synthetic Estrogens and Progestins on Glycogen Deposition in Female Mice,* Hormone Res. 21, pp. 199–203 (1985).

E.H. Leitzer et al; *Androgenic and Estrogenic Metabolites in Serum of Mice Fed Dehydroepiandrosterone: Relationship to Antihyperglycemic Effects,* Metabolism 36 No. 9, pp. 863–869 (1987).

J. N. Wright and M. Akhtar; *Studies on Estrogen Biosynthesis using Radioactive and Stable Istopes;* Steroids 55, pp. 142–151 (Apr. 1990).

C.E.M. Griffiths, et al; *Topical tretinoin (retinoic acid) treatment of hyperpigmented lesions associated with photoaging in Chinese and Japanese patients: a vehicle–controlled trial;* Journal of American Academy of Dermatology 30 No. 1, pp. 76–84 (1994).

A. Basdevant et al; *Transdermal Estradiol,* New England Journal of Medicine 315 No. 24, (1986).

19-OXYGENATED STEROIDS AS THERAPEUTIC AGENTS

FIELD OF THE INVENTION

The present invention relates to methods of inducing a therapeutic response by administration of 19-oxygenated steroids. More particularly, the present invention relates to methods of inducing a therapeutic response by administration of 3,19-dioxygenated steroids.

BACKGROUND OF THE INVENTION

It is well known to those skilled in the art that in the body certain 19-oxygenated 3-oxo(hydroxy)-steroids represent biogeneric precursors of estrogen in tissues possessing the appropriate enzymes. See for example, P. Morand et al., Chem Rev 68:85 (1968). A number of references have employed selected steroids to induce specific therapeutic responses. For example, U.S. Pat. No. 4,078,060 to Benson et al. proposes the use of androst-4-ene-3,17-diones for use in methods of inducing an estrogenic response. U.S. Pat. No. 4,096,254 to Benson et al. proposes methods of treating the primary symptoms of menopause and post-menopausal osteoporosis by administering androst-4-ene-3,17-diones. U.S. Pat. No. 4,078,061 also to Benson et al. proposes compounds useful for the treatment of acne which include 19-hydroxy-androst-4-ene-3,17-diones. U.S. Pat. No. 4,088,760 to Benson et al., proposes testosterone 5α-reductase inhibitors, also for the treatment of acne and oily skin. U.S. Pat. No. 4,317,818 to Benson et al. proposes 19-hydroxyandrost-4-ene-3,17-diones for the treatment of prostatic carcinoma. U.S. Pat. No. 4,055,641 to Benson et al. proposes 19-hydroxyandrost-4-ene-3,17-diones for the treatment of benign prostatic hypertrophy. U.S. Pat. No. 4,054,651 to Benson et al. proposes 19-hydroxyandrost-4-ene-3,17-diones as a method of contraception. U.S. Pat. No. 4,139,617 to Grunwell et al. proposes the use of 19-oxygenated-androst-5-enes for the enhancement of libido. Grunwell et al. specifically states that these compounds possess the property of "enhancing a diminished libido in mammals without evoking any overt androgenic or estrogenic response upon the secondary sex structures." U.S. Pat. No. 4,071,625 to Grunwell et al. proposes the use of 19-oxygenated-5α-androstanes for the enhancement of libido. U.S. Pat. Nos. 4,071,624 and 4,022,769 to Grunwell et al. propose the use of androst-4-en-19-ones for the enhancement of libido.

The present invention provides 3,19-dioxygenated derivatives of androstene and androstadiene for a variety of therapeutic applications. The steroids employed in the present invention are virtually devoid of hormonal properties on secondary sex characteristics, and have minimal binding affinities for the androgen and estrogen receptors, do not produce uterotrophic effects when administered parenterally, and possess minimal thrombosis-inducing properties.

SUMMARY OF THE INVENTION

The present invention provides as a first aspect, a method of inducing any of a variety of therapeutic responses. The method includes administering, to a subject in need of such a treatment, a compound of Formula (I)

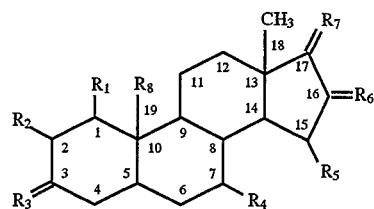

wherein:

R₁ is selected from the group consisting of H and α-loweralkyl;

R₂ is selected from the group consisting of H and β-OH;

R₃ is selected from the group consisting of O, H.β-OH, and H.β-OR₉;

R₄ is selected from the group consisting of H and α-loweralkyl;

R₅ is selected from the group consisting of H and β-OH;

R₆ and R₇ are each independently selected from the group consisting of H₂, O, H.OH, H.OR₉, and R₁₀.OH;

R₈ is selected from the group consisting of CHO, CH₂OH, CH(OH)₂, CH₂OR₉ and CH(OR₉)₂;

R₉ is selected from the group consisting of acyl having from 1 to 12 carbon atoms, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms;

R₁₀ is selected from the group consisting of loweralkyl, loweralkenyl, and loweralkynyl;

and wherein said compound of Formula (I) is ethylenically unsaturated at a set of locations selected from the group consisting of (a) between C₄ C₄ and C₅; (b) both between C₃ and C₄ and between C₅ and C₆; (c) between C₅ and C₆; (d) both between C₄ and C₅ and between C₆ and C₇; (e) both between C₃ and C₄ between C₅ and C₆ and between C₇ and C₈; (f) both between C₄ and C₅ and between C₇ and C₈; and (g) both between C₅ and C₆ and between C₇ and C₈. The compound of Formula (I) is administered in an amount effective to induce the desired therapeutic response. The methods claimed herein specifically exclude the subject matter described in the Benson et al. references discussed hereinabove.

As a second aspect, the present invention provides a method of treating the photoaging of skin in a subject in need thereof, comprising administering a compound of Formula (I) to the subject in an amount effective to treat the photoaging of skin.

As a third aspect, the present invention provides a method of treating post-menopausal skin aging in a subject in need thereof comprising administering a compound of Formula (I) to the subject, in an amount effective to treat post-menopausal skin aging.

As a fourth aspect, the present invention provides a method of treating acne or oily skin in a subject in need thereof comprising administering a compound of Formula (I) to the subject, in an amount effective to treat acne or oily skin.

As a fifth aspect, the present invention provides a method of treating pattern baldness or alopecia in a subject in need thereof, comprising administering a compound of Formula (I) to the subject in an amount effective to treat pattern baldness or alopecia.

As a sixth aspect, the present invention provides a method of inducing a tissue-specific estrogenic response in a subject in need thereof, comprising administering a compound of Formula (I) to the subject in an amount effective to induce an estrogenic response.

As a seventh aspect, the present invention provides a method of treating arthritis or rheumatoid arthritis in a subject in need thereof, comprising administering a compound of Formula (D to the subject in an amount effective to treat arthritis or rheumatoid arthritis.

As a eighth aspect, the present invention provides a method of inducing a corticoid sparing effect in a subject in need thereof, comprising administering a compound of Formula (I) to the subject in an amount effective to induce a corticoid sparing effect.

As a ninth aspect, the present invention provides a method of stimulating the reticuloendothelial system in a subject in need thereof, comprising administering a compound of Formula (I) to the subject in an amount effective to stimulate the reticuloendothelial system of the subject.

As a tenth aspect, the present invention provides a method of treating insulin-related disorders, such as diabetes or hypoglycemia, which are associated with decreased pancreatic β cell degranulation in a subject in need of such treatment, comprising administering a compound of Formula (I) to the subject in an amount effective to treat insulin-related disorders.

The foregoing and other aspects of the present invention are explained in detail in the detailed description set forth below.

DETAILED DESCRIPTION OF THE INVENTION

As used herein, the term "loweralkyl" means a linear or branched alkyl group with 1–7 carbon atoms, such as for example, methyl, ethyl, propyl, isopropyl, n-butyl, s-butyl, t-butyl, isoamyl, n-pentyl, and n-hexyl. This definition also applies to the loweralkenyl, and loweralkoxy moieties. Illustrative of the alkenyl groups which can be present are the vinyl, allyl, 1-butenyl, 1-pentenyl, and 1-hexenyl radicals. The term "loweralkynyl" as used herein refers to a linear or branched alkynyl group having 1–6 carbon atoms. Illustrative of the alkynyl groups which can be present are the ethynyl, 1-propynyl and 1-butynyl radicals. The term "loweracyl" as used herein refers to a linear or branched acyl group with 1–10 carbon atoms. The terms "halo" and "halogen" as used herein refer to a substituent which may be fluoro, or chloro. Where no stereochemical designation (i.e., α or β) is specified for a given substituent, the substituent may exist in either the α or β forms, as will be appreciated by one skilled in the art.

As noted above, the methods of the present invention include administering a compound of Formula (I)

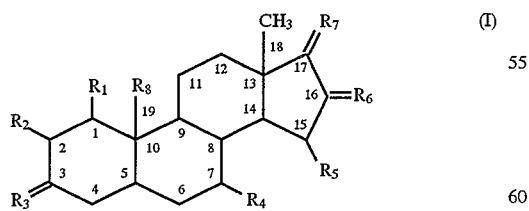

wherein:

$R_1$ is selected from the group consisting of H and α-loweralkyl;

$R_2$ is selected from the group consisting of H and β-OH;

$R_3$ is selected from the group consisting of O, H.β-OH, and H.β-OR$_9$;

$R_4$ is selected from the group consisting of H and α-loweralkyl;

$R_5$ is selected from the group consisting of H and β-OH;

$R_6$ and $R_7$ are each independently selected from the group consisting of $H_2$, O, H.OH, H.OR$_9$, and $R_{10}$.OH;

$R_8$ is selected from the group consisting of CHO, $CH_2OH$, $CH(OH)_2$, $CH_2OR_9$ and $CH(OR_9)_2$;

$R_9$ is selected from the group consisting of acyl having from 1 to 12 carbon atoms, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms;

$R_{10}$ is selected from the group consisting of loweralkyl, loweralkenyl, and loweralkynyl;

and wherein said compound of Formula (I) is ethylenically unsaturated at a set of locations selected from the group consisting of (a) between $C_4$ and $C_5$; (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and between $C_7$ and $C_8$.

One skilled in the art will appreciate that the ethylenic unsaturation occurs in the A and B rings. The following AB ring structures illustrate preferred locations of ethylenic unsaturation.

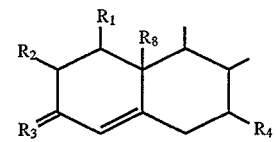
a

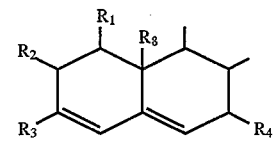
b

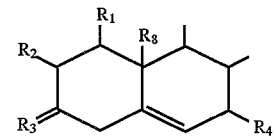
c

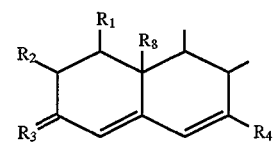
d

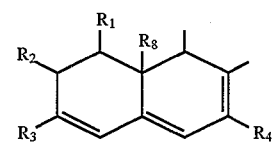
e

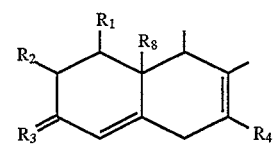
f

-continued

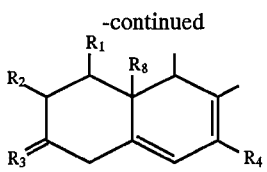

In one preferred embodiment, the compound of Formula (I) has the ethylenic unsaturation of structure b, and $R_3$ is H.β-$OR_9$. In another preferred embodiment, the compound of Formula (I) has the ethylenic unsaturation of structure d, and $R_3$ is β-$OR_9$. In one preferred embodiment, the compound of Formula (I) has the ethylenic unsaturation of structure g, $R_2$ is β-OH and $R_3$ is O.

Examples of preferred compounds of Formula (I) include compounds of Formula (I-A)

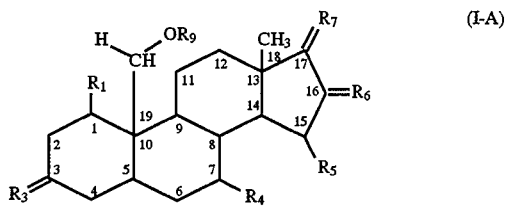

compounds of Formula (I-B)

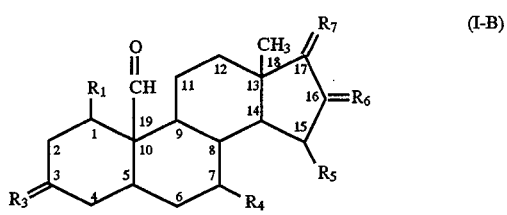

and compounds of Formula (I-C)

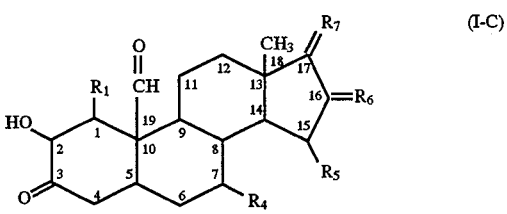

These compounds may be ethylenically unsaturated as described above.

In one embodiment, preferred compounds of Formula (I) are those compounds wherein $R_3$ is selected from the group consisting of H.β-OH, and H.β-$OR_9$. In one embodiment, preferred compounds of Formula (I) are those compounds wherein $R_3$ is O and $R_1$ is a α-loweralkyl. In one embodiment, preferred compounds of Formula (I) are those compounds wherein $R_3$ is O and $R_2$ is β-OH. In one embodiment, preferred compounds of Formula (I) are those compounds wherein $R_3$ is O and $R_4$ is α-loweralkyl. In one embodiment, preferred compounds of Formula (I) are those compounds wherein $R_3$ is O and $R_5$ is OH. In one embodiment, preferred compounds of Formula (I) are those compounds wherein $R_3$ is O and $R_6$ is selected from the group consisting of O, H.OH, H.$OR_9$, and $R_{10}$.OH. In one embodiment, preferred compounds of Formula (I) are those compounds wherein $R_3$ is O and $R_7$ is selected from the group consisting of $H_2$, $R_{10}$.OH, and H.$OR_9$ wherein $R_9$ is selected from the group consisting of 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms.

In one embodiment, preferred compounds of Formula (I) are those compounds wherein $R_3$ is O and $R_8$ is $CH_2(OR_9)$ wherein $R_9$ is selected from the group consisting of 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms.

When the symbol $R_3$ represents H.β-$OR_9$ and $R_9$ represents acyl, an acyl ester derived from a monobasic alkyl or aralkyl carboxylic acid having from 1 to 12 carbon atoms is present at the 3-position. The carboxylic acids from which these acylates are derived include saturated and unsaturated aliphatic acids as well as aromatic acids, as for example, acetic, propionic, butyric, isobutyric, valetic, isovaleric, caproic, caprylic, decanoic, dodecanoic, acrylic, crotonic, cyclobutanecarboxylic, cylcopentanecarboxylic, cyclopentenecarboxylic, cyclohexanecarboxylic, benzoic, toluic, naphthoic, ethylbenzoic, phenylacetic, naphthaleneacetic, phenylvaleric, cinnamic, phenylpropionic, p-propyloxyphenylpropionic and p-butyloxyphenylacetic acid.

When $R_7$ represents an oxo radical (O), the compounds of Formula (I) include substituted androst-5-en-17-ones. When $R_7$ represents H.$OR_9$ and $R_9$ represents acyl, a carboxylic acyl ester similar to those specifically described above for the 3-position is present.

$R_8$ delineates the type of oxygenated function present at the $C_{19}$ position. Thus, when $R_8$ is $CH_2OH$ the class of androst-5-en-19-ols is defined. When $R_8$ represents $CH_2OR_9$, and $R_9$ represents an acyl group having from 1 to 12 carbon atoms, the compounds of Formula (I) are a class of esters similar to those described above for the 3-position, as for example, androst-5-en-19-ol acylates. When $R_8$ represents CHO, androst-5-en-19-ones are defined.

A preferred group of compounds included within the scope of the present invention is the class of 3β-alcohols, and esters of androst-5-en-19-ol. These compounds are delineated where $R_3$ is H.β-OH or H.β-$OR_9$ and $R_9$ is acyl having from 1 to 12 carbon atoms, 2-tetrahydropyranyl, 4-tetrahydropyranyl, 1-cycloalkenyl having from 5 to 7 carbon atoms 1-methoxycycloalkyl and 1-ethoxycycloalkyl in which the cycloalkyl group has from 5 to 7 carbon atoms. Additionally, $R_8$ must be $CH_2OH$ in order to define the 19-hydroxy group.

Illustrative species which are encompassed within the preferred group of compounds include 3β-hydroxy-17α-methylandrost-5-ene-17β, 19-diol, 3β,17β-di(1'-cyclopentenyloxy)-17α-vinylandrost-5-en-19-ol, 17α-ethyl-3β-(1'-methoxycyclopentyloxy), 3β,19-dihydroxy-7α-methylandrost-5-en-17-one 3-acetate, 3β-(1'-cycloheptenyloxy) androst-5-ene-17β, 19-diol, 17-propionate, 17α-(1'-ethynyl)-3β, 17β-diisopropoxy-7α-methylandrost-5-en-19-ol, 17β-(1'-ethoxycycloheptyloxy)-17α-ethyl-4α, 7α-dimethylandrost-5-ene-3β, 19-diol 3-acetate, 3β-ethoxy-19-hydroxy-androst-5-en-17-one, 17β-ethoxy-17α-hexyl-3β-tributylsiloxyandrost-5-en-19-ol, 3β, 19-dihydroxy-7α-methylandrost-5-en-17-one, 17α-butyl-3β-(1'-methoxycyclohexyloxy)-1α, 7α-dimethylandrost-5-ene-17β, 19-diol, 17-decanoate, and 3β,19-dihydroxy-androst-5-en-17-one 3-propionate.

Another preferred group of compounds included within the scope of the present invention is the class of compounds of Formula (I) wherein $R_3$ is H.β-$OR_9$, wherein $R_9$ is acyl, and the AB rings are ethylenically unsaturated at the set of locations including (a) between $C_3$ and $C_4$ and between $C_5$ and $C_6$, and (b) between $C_3$ and $C_4$, between $C_5$ and $C_6$, and between $C_7$ and $C_8$. These compounds are the enol ethers or enol acylates of the corresponding unsaturated ketones wherein $R_3$ is oxo (O). The enol ethers or enol acylates possess the same basic biological activities as their precursor ketones, but vary in their lipophilic solubilities, thus rendering them more potent and/or longer acting.

Illustrative species which are encompassed within this preferred group of compounds include 3β-hydroxy-1β-methyl-17β-(2'-tetrahydropyranyloxy) androst-5-en-19-one, 3β, 17β-di(4'-tetrahydropyranyloxy)-17α-vinylandrost-5-en- 19-one, 3β-hydroxy-17β-hydroxyandrost-5-en-19-one, 3β-hydroxy-17α-(ethynyl)-17β-hydroxy-7α-methylandrost-5-en-19-one, 3-acetate, 17α-ethyl-3β, 17β-diisopropoxy-4α, 7α-dimethylandrost-5-en-19-one, 3β-hydroxyandrost-5-ene-17, 19-dione, 3-acetate, 7α-methyl-3β-propoxyandrost-5-ene-17, 19-dione, 17α-butyl-3β, 17β-dihydroxy-1α, 7α-dimethylandrost-5-en-19-one, 17β-decanoate, 3β, 17β-di(1'-cyclopentenyloxy)-4α, and 6-dimethyl-17α-(1'-propenyl)androst-5-en-19-one.

Generally, the compounds according to Formula (I) are known in the art. All compounds of Formula (I) may be prepared according to methods known to those skilled in the art.

The compounds of Formula (I) are useful for a variety of therapeutic purposes. The present invention provides a method of inducing a therapeutic response in a subject, comprising administering a compound of Formula (I) in an amount effective to induce the desired therapeutic response. The preferred compounds for inducing a therapeutic response include compounds of Formula (I) wherein the variables $R_1$ through $R_{10}$ have the meanings described above and the AB rings may be ethylenically unsaturated as described above, but with the proviso that when $R_2$ is H and $R_3$ is oxo (O), the compound of Formula (I) is ethylenically unsaturated at a set of locations selected from the group consisting of (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and between $C_7$ and $C_8$. In one embodiment, preferred compounds of Formula (I) for use in methods of inducing therapeutic responses according to the present invention include compounds of Formula (I) wherein $R_3$ is selected from the group consisting of H.β-OH, and H.β-OR$_9$. In one preferred embodiment $R_3$ is oxo (O) and the compound of Formula (I) is ethylenically unsaturated between $C_4$ and $C_5$ and between $C_6$ and $C_7$. In one preferred embodiment, $R_2$ is OH and $R_7$ is $R_{10}$.OH, preferably $R_{10}$.β-OH. In one preferred embodiment, $R_3$ is H.β-OH, $R_7$ is oxo (O), and $R_8$ is H.OH. In one preferred embodiment, $R_7$ is H.OH, preferably H.β-OH. In one preferred embodiment, $R_6$ is H.OH, preferably H.α-OH, and $R_7$ is H.OH, preferably H.β-OH.

As will be appreciated by one skilled in the art, the specific amount of the compounds of Formula (I) to be administered will depend upon a number of factors, including but not limited to the particular compound of Formula (I) selected, the particular therapeutic response desired, the sensitivity of the subject to the therapeutic effects of the particular compound of Formula (I) selected, and many other well known factors. Generally, the amount of compounds of Formula (I) to be administered is a therapeutically effective, but non-fatal amount. Typically, the compounds of Formula (I) are administered in an amount of between about 1 mg and 2 mg daily, up to about 0.5 g daily.

The compounds of Formula (I) are particularly useful in methods of treating the photoaging and other actinic changes of the skin, such as for example, wrinkling, premature aging, and irregular thinning of the epidermis. The photoaging of skin may also lead to the appearance of discrete hyperpigmented lesions which can be very troublesome, particularly in Chinese, Japanese, and other Oriental skin types. Treatments to relieve these conditions often employ retinoin (retinoic acid) cream and abrasion techniques which are often associated with skin irritation. As an alternative, the methods of the present invention comprise administering a compound of Formula (I) in an amount effective to treat the photo-aging of skin. Preferably, the compounds of Formula (I) are administered topically.

In one embodiment, the method of the present invention includes administering a compound of Formula (I) wherein $R_3$ is H.β-OH. In one embodiment, the method includes administering a compound of Formula (I) wherein $R_1$ and $R_5$ are H. In one embodiment, the method includes administering a compound of Formula (I) wherein $R_7$ is oxo (O). In one embodiment, the method includes administering a compound of Formula (I) wherein $R_8$ is $CH_2OH$. In one embodiment, the method includes administering a compound of Formula (I) wherein $R_8$ is $CH_2OR_9$. In one embodiment, the method includes administering a compound of Formula (I) wherein $R_3$ is H.β-OR$_9$. In one particularly preferred embodiment, the compound of Formula (I) is 19-hydroxydehydroepiandrosterone.

As will be appreciated by one skilled in the art, the methods of the present invention for treating the photo-aging of skin may further include administering the compound of Formula (I) in admixture, or concomitantly with a second agent known to be useful in the treatment of the photo-aging of skin. One skilled in the art will appreciate that such admixtures or concomitant administration techniques are contemplated by the present invention. For example, in one preferred embodiment of the method of the present invention for the treatment of photo-aging of skin, the compound of Formula (I) is administered concomitantly with retinoic acid or other known retinoid derivatives.

The compounds of Formula (I) are also useful in methods of treating post-menopausal skin aging in a subject in need thereof. Examples of conditions associated with post-menopausal skin aging which may be treated according to methods of the present invention include but are not limited to the loss of tension and elasticity; degerative changes in the vasculature synthesis and metabolism; reduction in water holding capacity of the stratum corneum and its dryness (xerosis) causing wrinkle formation, brown spots, skin laxity, related bags and blotches, irregular distribution of skin color, yellowish or orange discoloration, leather-like appearance, and the like. The methods include administering a compound of Formula (I) in an amount effective to treat post-menopausal skin aging. The preferred compounds for treating post menopausal skin aging include compounds of Formula (I) wherein the variables $R_1$ through $R_{10}$ have the meanings described above and the AB rings may be ethylenically unsaturated as described above, but with the proviso that when $R_2$ is H and $R_3$ is oxo (O), the compound of Formula (I) is ethylenically unsaturated at a set of locations selected from the group consisting of (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and between $C_7$ and $C_8$.

In one embodiment, the method of the present invention includes administering a compound of Formula (I) wherein $R_3$ is H.β-OH. In one embodiment, the method includes administering a compound of Formula (I) wherein $R_3$ is oxo (O) and the compound of Formula (I) is ethylenically unsaturated between $C_4$ and $C_5$ and between $C_6$ and $C_7$. In one embodiment, the method includes administering a compound of Formula (I) wherein $R_1$ and $R_5$ are H. In one embodiment, the method includes administering a compound of Formula (I) wherein $R_7$ is oxo (O). In one embodiment, the method includes administering a compound of Formula (I) wherein $R_a$ is $CH_2OH$. In one embodiment, the method includes administering a compound of Formula (I) wherein $R_8$ is $CH_2OR_9$. In one embodiment, the method includes administering a compound of Formula (I) wherein $R_3$ is H.β-$OR_9$. In one particularly preferred embodiment, the compound of Formula (I) is 19-hydroxydehydroepiandrosterone.

As will be appreciated by one skilled in the art, the methods of the present invention for treating post-menopausal skin aging may further include administering the compound of Formula (I) in admixture, or concomitantly with a second agent known to be useful in the treatment of the post-menopausal skin aging. One skilled in the art will appreciate that such admixtures or concomitant administration techniques are contemplated by the present invention. For example, in one preferred embodiment of the method of the present invention for the treatment of post-menopausal skin aging, the compound of Formula (I) is administered concomitantly with 3β,17β-dihydroxy-5-androstene. In another preferred embodiment, the method of treating post-menopausal skin aging comprising administering the compound of Formula (I) concomitantly with retinoic acid.

The compounds of Formula (I) are also useful in methods of treating acne or oily skin in subjects in need thereof. The methods include administering a compound of Formula (I) in an amount effective to treat acne or oily skin. The preferred compounds for treating acne or oily skin include compounds of Formula (I) wherein the variables $R_1$ through $R_{10}$ have the meanings described above and the AB rings may be ethylenically unsaturated as described above, but with the proviso that when $R_2$ is H and $R_3$ is oxo (O), the compound of Formula (I) is ethylenically unsaturated at a set of locations selected from the group consisting of (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and between $C_7$ and $C_8$.

In one embodiment, the method of the present invention includes administering a compound of Formula (I) wherein $R_3$ is H.β-OH. In one embodiment, the method includes administering a compound of Formula (I) wherein $R_3$ is oxo (O) and the compound of Formula (I) is ethylenically unsaturated between $C_4$ and $C_5$ and between $C_6$ and $C_7$. In one embodiment, the method of the present invention includes administering a compound of Formula (I) wherein $R_1$ and $R_5$ are H. In one embodiment, the method includes administering a compound of Formula (I) wherein $R_7$ is oxo (O). In one embodiment, the method includes administering a compound of Formula (I) wherein $R_8$ is $CH_2OH$. In one embodiment, the method includes administering a compound of Formula (I) wherein $R_8$ is $CH_2OR_9$. In one embodiment, the method of the present invention includes administering a compound of Formula (I) wherein $R_3$ is H.β-$OR_9$. In one particularly preferred embodiment, the compound of Formula (I) is 19-hydroxydehydroepiandrosterone.

As will be appreciated by one skilled in the art, the methods of the present invention for treating acne or oily skin may further include administering the compound of Formula (I) in admixture, or concomitantly with a second agent known to be useful in the treatment of acne or oily skin. For example, the compounds of Formula (I) may be administered with retinoic acid. According to another preferred embodiment, the compounds of Formula (I) may be administered with 5α-reductase inhibitors and/or other antiandrogens such as those described in G. Rasmusson, et al., *Annual Reports in Medicinal Chemistry* 29:225 (1994), the subject matter of which is incorporated herein by reference in its entirety. One skilled in the art will appreciate that such admixtures or concomitant administration techniques are contemplated by the present invention.

The compounds of Formula (I) are also useful in methods of treating pattern baldness or alopecia in subjects in need thereof. The methods include administering a compound of Formula (I) in an amount effective to treat pattern baldness or alopecia. Advantageously, the compounds of Formula (I) may be administered to subjects afflicted with pattern baldness to treat such condition without the systemic effects associated with previously known treatments, such as administration of estrogens. For example, treatment of pattern baldness in males with estrogen has been associated with gynecomastia, which systemic effect is avoided by the use of the compounds of Formula (I). The preferred compounds for the treatment of pattern baldness and alopecia include compounds of Formula (I) wherein the variables $R_1$ through $R_{10}$ have the meanings described above and the AB rings may be ethylenically unsaturated as described above, but with the proviso that when $R_2$ is H and $R_3$ is oxo (O), the compound of Formula (I) is ethylenically unsaturated at a set of locations selected from the group consisting of (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and between $C_7$ and $C_8$.

In one embodiment, the method of the present invention includes administering a compound of Formula (I) wherein $R_3$ is H.β-OH. In one embodiment, the method includes administering a compound of Formula (I) wherein $R_3$ is oxo (O) and the compound of Formula (I) is ethylenically unsaturated between $C_4$ and $C_5$ and between $C_6$ and $C_7$. In one embodiment, the method of the present invention includes administering a compound of Formula (I) wherein $R_1$ and $R_5$ are H. In one embodiment, the method includes administering a compound of Formula (I) wherein $R_7$ is oxo (O). In one embodiment, the method includes administering a compound of Formula (I) wherein $R_8$ is $CH_2OH$. In one embodiment, the method includes administering a compound of Formula (I) wherein $R_8$ is $CH_2OR_9$. In one embodiment, the method of the present invention includes administering a compound of Formula (I) wherein $R_3$ is H.β-$OR_9$. In one particularly preferred embodiment, the compound of Formula (I) is 19-hydroxydehydroepiandrosterone.

As will be appreciated by one skilled in the art, the methods of the present invention for treating pattern baldness or alopecia may further include administering the compound of Formula (I) in admixture, or concomitantly with a second agent known to be useful in the treatment of pattern baldness or alopecia. For example, the compounds of Formula (I) may be administered with cyclosporins. According to another preferred embodiment, the compounds of Formula (I) may be administered with 5α-reductase inhibitors and/or other antiandrogens. One skilled in the art will appreciate that such admixtures or concomitant administration techniques are contemplated by the present invention.

The present invention also provides methods of inducing other tissue-specific estrogenic responses in a subject, comprising administering a compound of Formula (I) in an amount effective to induce an estrogenic response. As noted above, the methods of the present invention are advantageous in that the compounds of Formula (I) are not associated with producing the systemic effects associated with administering estrogens. The estrogenic responses produced by the compounds of Formula (I) are specific to tissues which contain the complex enzymatic machinery capable of metabolizing the compounds of Formula (I) to estrogen. Accordingly, the estrogenic responses occur in those tissues which contain the aromatase enzymes. The administration of the compounds of Formula (I) does not result in the systemic effects associated with the administration of estrogen because the compounds of Formula (I) only produce estrogenic responses in these specific tissues. Accordingly, there is no estrogenic response produced when the compounds of Formula (I) are present in tissues which do not contain aromatase and therefore are incapable of converting the compounds of Formula (I) to estrogen. Tissues in which significant estrogenic responses occur include but are not limited to the scalp, abdominal and breast fat, and hypothalmic and limbic systems in the brain, skin and kidney. Locations in which estrogenic response do not occur to a significant extent include the blood stream, the uterus, and the breasts.

The preferred compounds for inducing tissue-specific estrogenic responses include compounds of Formula (I) wherein the variables $R_1$ through $R_{10}$ have the meanings described above and the AB rings may be ethylenically unsaturated as described above, but with the proviso that when $R_2$ is H and $R_3$ is oxo (O), the compound of Formula (I) is ethylenically unsaturated at a set of locations selected from the group consisting of (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and $C_7$ and $C_8$. The administration of a compound of Formula (I) as described, may induce any of a variety of estrogenic responses. One skilled in the art will appreciate, that estrogens and androgens are often synergistic, and may induce a variety of hormonal responses. The term "estrogenic" as used herein refers to a response which is primarily estrogenic in nature, but which may be effected by estrogen alone, or by the synergistic interaction of estrogen and androgen.

Examples of estrogenic responses are known to those skilled in the art. For example, these compounds are useful for the treatment of a variety of conditions including treatment of hypogonadal women, inhibition of ovulation, or hormonal support of menopausal and post-menopausal women, treatment of menopausal disorders, treatment of atrophic vaginitis, and treatment of benign prostatic hypertrophy and prostatic carcinoma in men, as well as others known to those skilled in the art.

In one embodiment, the method of the present invention includes administering a compound of Formula (I) wherein $R_3$ is H.β-OH. In one embodiment, the method includes administering a compound of Formula (I) wherein $R_3$ is oxo (O) and the compound of Formula (I) is ethylenically unsaturated between $C_4$ and $C_5$ and between $C_6$ and $C_7$. In one embodiment, the method of the present invention includes administering a compound of Formula (I) wherein $R_1$ and $R_5$ are H. In one embodiment, the method includes administering a compound of Formula (I) wherein $R_7$ is oxo (O). In one embodiment, the method includes administering a compound of Formula (I) wherein $R_8$ is $CH_2OH$. In one embodiment, the method includes administering a compound of Formula (I) wherein $R_8$ is $CH_2OR_9$. In one embodiment, the method of the present invention includes administering a compound of Formula (I) wherein $R_3$ is H.β-$OR_9$. In one particularly preferred embodiment, the compound of Formula (I) is 19-hydroxydehydroepiandrosterone.

As will be appreciated by one skilled in the art, the methods of the present invention for inducing any of the foregoing estrogenic response may further include administering the compound of Formula (I) in admixture, or concomitantly with a second agent known to be useful in the treatment of the particular condition. For example, the treatment of benign prostatic hypertrophy and prostatic cancer is generally improved by using a product of the present invention together with an androgen antagonist such as 5α-reductase inhibitors. One skilled in the art will appreciate that such admixtures or concomitant administration techniques are contemplated by the present invention.

The compounds of Formula (I) are also useful in methods of treating arthritis or rheumatoid arthritis. The present invention provides methods of treating arthritis or rheumatoid arthritis in a subject, comprising administering a compound of Formula (I) in an amount effective to treat arthritis or rheumatoid arthritis. In one embodiment, preferred compounds of Formula (I) for use in methods of treating arthritis or rheumatoid arthritis according to the present invention include compounds of Formula (I) wherein $R_7$ is selected from the group consisting of oxo (O) and H.OH, preferably H.β-OH. In one preferred embodiment, $R_6$ is H.OH, preferably H.β-OH, and $R_7$ is H.OH, preferably H.β-OH. In one preferred embodiment, $R_3$ is H.β-$OR_9$. In one preferred embodiment, $R_3$ is H.βOH, $R_6$ is H.OH, preferably H.α-OH, and $R_7$ is H.OH, preferably H.β-OH. In one particularly preferred embodiment, the compound of Formula (I) is 16-epiestriol.

According to one preferred embodiment, the method of treating arthritis or rheumatoid arthritis comprises administering a compound of Formula (I) in admixture with an anti-inflammatory agent. Suitable anti-inflammatory agents are well known in the art, and include but are not limited to, corticoids, and non-steroidal anti-inflammatory drugs.

The compounds of Formula (I) are also useful for inducing a corticoid sparing effect in endogenous or exogenous corticoids. "Corticoid sparing effect" means that the effects of the corticoids are increased as compared to effects seen without the administration of compounds of Formula (I). In this manner, a subject in need of corticoid therapy may achieve the same beneficial effect with less corticoid compound, thereby reducing the risk of skin atrophy and other adverse side effects associated with the administration of corticoids. The present invention provides a method of inducing a corticoid sparing effect in a subject comprising administering a compound of Formula (I) in an amount effective to induce the sparing effect. In one preferred embodiment, the compounds of Formula (I) are administered adjunctively with one or more corticosteroids.

The present invention also provides a method of stimulating the reticuloendothelial system in a subject, comprising administering a compound of Formula (I) in an amount effective to stimulate the reticuloendothelial system of the subject. Stimulation of the reticuloendothelial systems is beneficial for the treatment of athereosclerosis. In one embodiment, preferred compounds of Formula (I) for use in methods of stimulating the reticuloendothelial system of a subject according to the present invention include compounds of Formula (I) wherein $R_6$ is selected from the group consisting of O and H.OH. In one preferred embodiment, $R_7$ is H.OH, preferably H.β-OH. In one preferred embodiment, $R_6$ is H.OH, preferably H.α-OH, and $R_7$ is H.OH, preferably H.β-OH. In one preferred embodiment, $R_8$ is CHO.

The present invention also provides methods of treating insulin related disorders including diabetes and hypoglycemia. The specific types of insulin-related disorders which may be treated according to the methods of the present invention include conditions associated with decreased pancreatic β cell degranulation. The method of the present invention comprises administering a compound of Formula (I) in an amount effective to treat the specific insulin-related disorder. In one embodiment, preferred compounds of Formula (I) for use in methods of treating insulin-related disorders in a subject according to the present invention include compounds of Formula (I) wherein $R_6$ is selected from the group consisting of O and H.OH. In one preferred embodiment, $R_7$ is H.OH, preferably H.β-OH. In one preferred embodiment, $R_6$ is H.OH, preferably H.α-OH, and $R_7$ is H.OH, preferably H.β-OH. In one preferred embodiment, $R_3$ is H.β-$OR_9$. In one preferred embodiment, $R_5$ is selected from the group consisting of CHO and $CH_2OH$.

The compounds useful in the methods of the present invention may be provided in formulations suitable for oral, rectal, intravaginal, topical, buccal (e.g., sub-lingual), intranasal, parenteral (e.g., subcutaneous, intramuscular, intradermal, or intravenous), transdermal administration, and systemic, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined mount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients). In general, the formulations of the invention are prepared by uniformly and intimately admixing the active compound with a liquid or finely divided solid carrier, or both, and then if necessary, shaping the resulting mixture. For example, a tablet may be prepared by compressing or moulding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Moulded tablets may be made by moulding, in a suitable machine, the powdered compound moistened with an inert liquid binder. The oral administration of compounds of Formula (I) are preferred in the methods according to the present invention for the treatment of arthritis or rheumatoid arthritis, and for inducing a variety of estrogenic responses, including the treatment of acne or oily skin, the treatment of post-menopausal skin aging, the treatment of other menopausal disorders, and the treatment of benign prostatic hypotrophy and prostatic carcinoma.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood. The parenteral administration of compounds of Formula (I) are preferred in the methods according to the present invention for the treatment of arthritis or rheumatoid arthritis, and for inducing a variety of estrogenic responses, including the treatment of post-menopausal skin aging, and the treatment of other menopausal disorders.

Formulations suitable for rectal or intravaginal administration are preferably presented as unit dose suppositories. These may be prepared by admixing the active compound with one or more conventional solid carriers, for example, coca butter, and then shaping the resulting mixture. The intravaginal administration of compounds of Formula (I) are preferred in the methods according to the present invention for the inducement of a variety of estrogenic responses, including the treatment of menopausal disorders.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The topical administration of compounds of Formula (I) are preferred in the methods according to the present invention for inducing corticoid sparring effects, the treatment of photoaging of skin, and for inducing a variety of estrogenic responses, including the treatment of acne or oily skin, the treatment of post-menopausal skin aging, the treatment of other menopausal disorders, the treatment of vaginal atrophy, the inhibition of male pattern baldness, and the treatment of androgenic alopecia.

Formulations suitable for transdermal administration may be presented as discrete patches adapted to remain in intimate contact with the epidermis of the recipient for prolonged periods of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis/tris buffer (pH 6) or ethanol/water.

Any of the compounds of Formula (I) may be administered in any of the foregoing forms. It is currently preferred for most compounds of Formula (I), and most applications, that the compounds of Formula (I) be administered orally and/or topically. With respect to the compounds of Formula (I) wherein $R_3$ is oxo (O), it is currently preferred that the compounds be administered parenterally.

Any of the foregoing formulations may be employed for the systemic administration of compounds of Formula (I). The systemic administration of compounds of Formula (I) are preferred in methods according to the present invention for stimulating the reticuloendothelial system, for treatment of menopausal disorders, and for the treatment of benign prostatic hypotrophy and prostatic carcinoma.

The following examples are provided to illustrate the present invention, and should not be construed as limiting thereof. In these examples, "mg" means milligrams, "g" means grams, and "hr" means hour(s).

EXAMPLE 1

Three litters of four immature female rats age 27 days are employed. Each rat from each litter is given a daily dose of 19-hydroxydehydroepiandrosterone suspended in carboxymethycellulose solution by stomach tube, to assess uterotrophic and vaginal cornification. One rat from each litter is given 10.0 mg, 1.0 mg, and 0.1 mg (per 100 g body weight) respectively. The fourth rat from each litter is given vehicle only. Vaginal smears are made daily and the rats are euthenized on the 4th day.

One rat out of the three receiving the 10.0 mg dose daily had a cornified vaginal smear on the last day, and a pro-oestrus type smear on day 3. No other rats show signs of cornification.

The following table illustrates the data received upon examination of uterine weights.

TABLE 1

| Treatment | Uterine weight (mg/100 g) | Mean |
| --- | --- | --- |
| None | 58, 65, 251 | 125 |
| 0.1 mg/day | 72, 82, 112 | 88 |
| 1.0 mg/day | 81, 66, 46 | 64 |
| 10.0 mg/day | 126, 90, 80 | 99 |

The results indication that 19-hydroxydehydroepiandrosterone administered orally in doses of up to 10 mg/day is without significant estrogenicity as measured by uterotrophic effects.

EXAMPLE 2

Eight litters of four males are employed to determine the sebum secretion and androgen target effects of 19-hydroxydehydroepiandrosterone. Two rats from each litter are castrated and implanted with testosterone giving uptake of about 0.2 mg/day. The remaining two rats from each litter remained intact without implantation. One castrated and one intact rat from each litter are given 1.0 mg/Kg body weight of 19-hydroxydehydroepiandrosterone in carboxymethylcellulose solution daily. The remaining rats of each litter are given vehicle only.

Treatment is continued for 24 days. On day 16, the rats are shampooed and a sample of hair is taken from one flank. A further sample of hair is taken from the opposite flank on day 24. The lipid is extracted according to techniques described in F. G. Ebling, *ACTA Endocryinologica* 72:361 (1973), which permits estimations of lipid production over the 8-day period. The animals are euthenized and dissected on the 31st day after initiating treatment.

The results are reported in Table 2 below.

TABLE 2

| | Castrated w/ Testosterone | | Intact | |
| --- | --- | --- | --- | --- |
| Treatment | vehicle | drug | vehicle | drug |
| Sebum production[1] | 1.57 ± 0.16 | 0.83 ± 0.23 | 1.07 ± 0.09 | 1.08 ± 0.10 |
| Ventral prostate[2] | 207 ± 14 | 198 ± 17 | 84 ± 8 | 84 ± 5 |
| Seminal vesicles[2] | 392 ± 34 | 410 ± 47 | 203 ± 31 | 179 ± 16 |
| Preputial glands[2] | 49 ± 2.7 | 50 ± 3.9 | 29 ± 1.3 | 30 ± 1.3 |
| Testes[3] | — | — | 1.13 ± 0.022 | 1.19 ± 0.029 |
| Body weight[3] | 224 ± 8.7 | 226 ± 7.9 | 234 ± 9.8 | 234 ± 8.1 |

[1]Increase in hair fat (mg/g hair/24 hr) and relative weights (per 100 g body weight of androgen sensitive organs.
[2]Weight in mg.
[3]Weight in g.

The results indicate that lipid production in testosterone-implanted rats is reduced on average by 47% by the administration of 19-hydroxydehydroepiandrosterone. Thus, 19-hydroxydehydroepiandrosterone given orally at a dosage of 1.0 mg/day significantly reduces sebum secretion in castrated rats implanted with testosterone, but not in intact male rats.

19-hydroxydehydroepiandrosterone has no effect on the responses of three other targets to androgens, namely ventral prostate, seminal vesicles, and preputial glands. Thus there is no indication of anti-androgenicity. 19-hydroxydehydroepiandrosterone does not affect body weight, thus demonstrating that it is not systemically oestrogenic, and also does not affect testis weight, thus indicating that it does not suppress pituitary gonadotrophins.

Our findings indicate that orally administered 19-hydroxydehydroepiandrosterone, and metabolites thereof, inhibit sebum production without systemic estrogenicity, androgenicity, or general anti-androgenicity.

EXAMPLE 3

19-Hydroxyandrost-4-en-3-one 19 MEM ether 302 androstenedione, 186 mg MEM chloride (Carey et al., *Tet Letts* 11:809 (1976)), and 194 mg iPr NEt2, are combined in $CH_2Cl_2$ (1.86 ml). The mixture is stirred for 3 hours at room temperature and allowed to stand overnight. The product is purified with $CHCl_3$-hexane. The resulting compound has a m.p. of 200°–210° C.

EXAMPLE 4

19-Hydroxy $A_2$ 3-enol methyl ether

19 OH $A_2$ (1.0 g), 10 ml dioxan, 1.0 ml (MeO)3CH, and 0.1 g pTS are combined and stirred for 30 min. at room temperature. Pyridine (0.5 ml) is added in water. The product is collected and has a m.p. of 230°–265° C.

EXAMPLE 5

19-Hydroxy $A_2$ 19-benzoate 3-enol Me ether

19-OH $A_2$ (5.0 g) is heated with PhCOCl in pyridine for 2 hours with water. The crude product is converted to 3 enol-Me-ether, having a m.p. of 95°–96° C. The benzoate has a m.p. of 120°–122° C.

EXAMPLE 6

19-Hydroxy DHEA diacetate

19-OH DHEA (2.0 g), 4-$Me_2$-N-pyridine (0.2 g) and 5.0 ml $AC_2O$ are combined at room temperature. After several hours, water (20 ml) is added. The solution is mixed to decompose $Ac_2O$. The collected diacetate is pure and exhibits a m.p. of 104° C.

EXAMPLE 7

Aldol Condensation and 19-$OHA_2$ (19-$OCHOH_2.CCl_3$)

Powdered 19-$OHA_2$ (3 g), $C_6H_6$ (10 ml) and $CCl_3CHO$, prepared from 5 g chloroehydrate, are combined and allowed to stand overnight. The products is the evaporated to dryness and purified with acetone-pentane (N). The resulting compound has a m.p. of 175°–176° C.

EXAMPLE 8

17α-Ethynyl-19-OH testosterone

Potassium in 370 ml tetrahydrofuran are reacted under nitrogen. The product is treated over 1.5 hours with 400 ml t-BuOH, added in portions. When the potassium is solubilized, $C_2H_2$ is passed in for 2.5 hours. 3-OMe-19-OAc-3,5-en-17-one, dissolved in 150 ml THF is added. $C_2H_2$ is passed in with stirring for 4 more hours. The reaction is allowed to stand overnight. 20 g of concentrated HCl, diluted to 200 ml is added, and the mixture is left overnight. The product is isolated by the addition of $Et_2O$. The solid is purified from EtOH and exhibits a m.p. of 261°–265° C.

EXAMPLE 9

19-Acetoxytestosterone

3-Me ether of 19-OH $A_2$ acetate is reduced with $NaBH_4$ in aqueous MeOH. The product (3-Me,19-OAc-17-OH $\Delta^{3,5}$ androstadiene) is heated with 60% HAc on a water bath with water, and gives the 3-oxo-19-acetoxy-17/3-OH-4-androstene

EXAMPLE 10

17α-Ethynyl-19-hydroxy-DHEA

Sliced potassium (20 g) is added to 370 ml THF, and 300 ml of t-BuOH is added dropwise with stiring over 1.5 hours. Thereafter $C_2H_2$ is passed through for 30 minutes to saturate and assist in solubilizing any residual potassium. 19-OH DHEA (20 g) dissolved in 150 ml THF and 100 ml t-BuOH, is added. $C_2H_2$ is passed through with stirring for 12 hours. Concentrated HCl (54 ml), is diluted to 200 ml and added. The reaction is left standing overnight. The product is extracted with $Et_2O$ an purified from EtOH. The compound has a m.p. of 224°–225° C.

EXAMPLE 11

3-Ethoxy-3-5-androstadiene-17,-19-dione (i) To 19-OH-$A_2$ (11.1 g) in 300 ml acetone is added 9.9 ml Jones reagent [26.7 g $CrO_3$ in 23 ml concentrated $H_2SO_4$ diluted with ice to 100 ml] with rapid stiring. After a few minutes at room temperature the product is precipitated with water and the mixture is evaporated on a Rotovapor until an oil separates. The product is collected and recrystallized twice from aqueous MeOH. The product has a m.p. of 122°–124° C.

(ii) The 19-aldehyde (8 g) in 80 ml dioxane, 8 ml $(MeO)_3CH$, and 800 mg pTS are combined and stirred at room temperature for 30 min. Pyridine in slight excess is added and the product is precipitated with water. The product is recrystallized with aqueous MeOH containing a few drops of pyridine. 3-Enol-methyl-ether of the 19-aldehyde exhibits a m.p. of 143°–145° C.

The foregoing is illustrative of the present invention and is not to be construed as limiting thereof. The invention is defined by the following claims, with equivalents of the claims to be included therein.

EXAMPLE 12

19-Hydroxy-4-androstene-3,17-dione 19 MEM ether 19-hydroxy-4-androstene-3,17-dione (19-HO-$A_2$), (320 mg), 186 mg MEM chloride, 194 mg di-isopropylethylamine, and 1,86 ml methylene chloride are mixed in the above order, stirred for 3 hours and left overnight. The mixture is diluted with water and extracted with chloroform. The extract is washed with water, sodium bicarbonate solution, and water again, and then dried and evaporated. The product is crystallised from chloroform/light petroleum, and has a mp of 200°–210° C.

EXAMPLE 13

19-Hydroxy-4-androstene,3,17-dione-3-enol methyl ether

19-HO-$A_2$, (1.0 g) 10.0 ml dioxan, 1.0 ml trimethyl-orthoformate, and 100 mg pTS are stirred at room temperature for 30 min. Pyridine (1.0 ml) is added and the product is precipitated with water. After standing overnight in the refrigerator the solids are collected and dried. The product has a mp of 230°–265° C.

EXAMPLE 14

19-Hydroxy-4-androstene-3,17-dione 19-benzoate 3-enol methyl ether

19-HO-$A_2$ (5.0 g) in 25 ml pyridine is treated with 1.1 mole benzoyl chloride added dropwise with shaking at 0° C. After standing for 2 hours at 0° C. the product is precipitated with water and recrystallised from aqueous MeOH. The product has a Rhombs mp of 120°–122° C.

Benzoate (10.0 g), 100 ml dioxan, 10 ml trimethyl-orthoformate, and 500 mg pTS are stirred at room temperature for 30 min. Pyridine (2.5 ml) is added and the product is precipitated with water. After standing overnight in the refrigerator the solids are collected and dried. Recrystallisation from aqueous MeOH gives the pure product, having amp of 94°–95° C.

EXAMPLE 15

19-Hydroxy-dehydroepiandrosterone diacetate

19-Hydroxydehydroepiandrosterone (2.0 g), 200 mg 4-dimethylaminopyridine, and 5.0 ml acetic anhydride are mixed at room temperature. After several hours the product is precipitated with water, collected and dried. The resulting pure product has amp of 104° C.

EXAMPLE 16

19-(1',1',1'-trichloromethyl-2'-hydroxy)-ethoxy-4-androstene-3,17-dione

Chloral (Ca.3.0–3.5 ml) is prepared by carefully distilling 5 g chloral hydrate from 10 ml concentrated sulphuric acid under slightly reduced pressure. 19-HO-$A_2$ (3.0 g finely powdered) in 10 ml benzene is treated with the foregoing chloral and the mixture is stirred at room temperature and left overnight. The mixture is taken to dryness under reduced pressure and purified from acetone/hexane. The product has a mp of 175°–176° C.

EXAMPLE 17

17α-Ethynyl-19-hydroxytestosterone

Postassium metal (20 g) cut into small pieces is suspended in tetrahydrofuran (370 ml) under nitrogen and treated portionwise with tert-butanol (400 ml). When the potassium is largely dissolved acetylene is passed through the mixture. After 2.5 hours the 19-acetate-3-enol methyl ether of 19-HO-$A_2$ (21 g) in tetrahydrofuran (150 ml) is added and acetylene is passed through the mixture for another 12 hours. After leaving overnight at room temperature hydrochloric acid (20 g made up to 200 ml) is carefully added and the mixture is left overnight. The organic layer is decanted from the solids, which are washed with ether, and the total organic layer is evaporated to dryness in the ROTORVAPOR. The residue is treated with water and the insoluble material collected and purified from ethanol. The product has a mp of 261°–265° C.

EXAMPLE 18

19-Acetoxytestosterone

19-HO-$A_2$ 3-enol methyl ether 19-acetate (4 g), and 80 ml methanol are treated with stirring with a slight excess of sodium borohydride. When reduction is complete (tlc), acetone (10 ml) and 60% acetic acid (4 ml) are added and the mixture is heated on the water bath for 20 min. It is then evaporated on the ROTORVAPOR to small bulk and the product is precipitated with water and collected.

EXAMPLE 19

17α-Ethynyl-4-androstene-3β,17β,19-triol

Potassium metal (20 g), cut into small pieces, is suspended in tetrahydrofuran (370 ml) under nitrogen and treated portionwise with tert-butanol (400 ml). When the potassium is largely dissolved acetylene is passed through the mixture. After 2.5 hours 19-hydroxydehydroepiandrosterone (20 g) in tetrahydrofuran (150 ml) is added and acetylene is passed through the mixture for another 12 hours. After leaving overnight at room temperature hydrochloric acid (20 g made up to 200 ml) is carefully added and the mixture is left overnight. The organic layer is decanted from the solids, which are washed with ether, and the total organic layer is evaporated to dryness in the ROTORVAPOR. The residue is treated with water and the insoluble material is collected and purified from aqueous ethanol. The product has a mp of 224°–225° C.

EXAMPLE 20

3-Ethoxy-3,5-androstadiene-17,19-dione

To 19-HO-$A_2$ (11.1 g) in acetone (300 ml) is added Jones Reagent (9.9 ml) [chromic acid (20.7 g) dissolved in concentrated sulphuric acid (23 ml) and the solution diluted with ice to 100 ml] with rapid stirring. After a few minutes at room temperature the product is precipitated with water and the mixture evaporated on the ROTORVAPOR until an oil separated. The aqueous layer is removed by decantation and the residue is crystallised twice from aqueous MeOH. The product has a mp of 122°–124° C.

The foregoing 19-aldehyde (8 g) is dissolved in dioxan (80 ml), and trimethylorthoformate (8 ml) and pTS (800 mg) are added. The mixture is stirred at room temperature for 30 min. Pyridine in slight excess is added and the product is precipitated with water and collected. It is purified from aqueous methanol containing a few drops of pyridine. The product has a mp of 143°–145° C.

That which is claimed is:

1. A method of treating acne or oily skin in a subject in need thereof comprising administering to said subject, a compound of Formula (I)

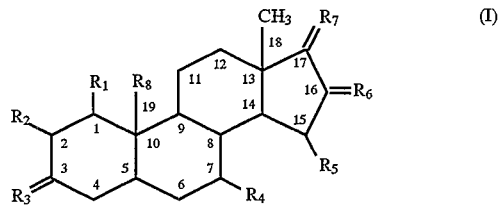

wherein:

$R_1$ is selected from the group consisting of H and α-loweralkyl;

$R_2$ is selected from the group consisting of H and β-OH;

$R_3$ is selected from the group consisting of O, H.β-OH, and H.β-$OR_9$;

$R_4$ is selected from the group consisting of H and α-loweralkyl;

$R_5$ is selected from the group consisting of H and β-OH;

$R_6$ and $R_7$ are each independently selected from the group consisting of $H_2$, O, H.OH, H.$OR_9$, and $R_{10}$.OH;

$R_8$ is selected from the group consisting of CHO, $CH_2OH$, $CH(OH)_2$, $CH_2OR_9$ and $CH(OR_9)_2$;

$R_9$ is selected from the group consisting of acyl having from 1 to 12 carbon atoms, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms;

$R_{10}$ is selected from the group consisting of loweralkyl, loweralkenyl, and loweralkynyl;

and wherein said compound of Formula (I) is ethylenically unsaturated at a set of locations selected from the group consisting of (a) between $C_4$ and $C_5$; (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and between $C_7$ and $C_8$;

subject to the proviso that when $R_2$ is H and $R_3$ is oxo (O), said compound of Formula (I) is ethylenically unsaturated at said set of locations selected from the group consisting of (b), (c), (d), (e), (f), and (g);

or a pharmaceutically acceptable salt, in an amount effective to treat acne or oily skin.

2. The method according to claim 1, wherein $R_1$ and $R_5$ are each H.

3. The method according to claim 1, wherein $R_7$ is O.

4. The method according to claim 1, wherein $R_8$ is selected from the group consisting of $CH_2OH$ and $CH_2OR_9$.

5. The method according to claim 1, wherein said compound of Formula (I) is administered concomitantly with retinoic acid.

6. The method according to claim 1, wherein said compound of Formula (I) is administered concomitantly with a 5α-reductase inhibitor.

7. A method of treating acne or oily skin in a subject in need thereof comprising administering to said subject, a compound of Formula (I)

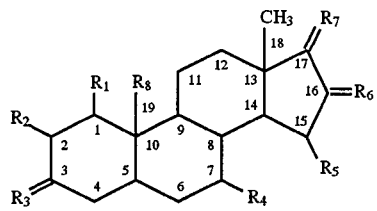

wherein:

$R_1$ is selected from the group consisting of H and α-loweralkyl;

$R_2$ is selected from the group consisting of H and β-OH;

$R_3$ is H.β-OH;

$R_4$ is selected from the group consisting of H and α-loweralkyl;

$R_5$ is selected from the group consisting of H and β-OH;

$R_6$ and $R_7$ are each independently selected from the group consisting of $H_2$, O, H.OH, H.OR$_9$, and $R_{10}$.OH;

$R_8$ is selected from the group consisting of CHO, $CH_2OH$, $CH(OH)_2$, $CH_2OR_9$ and $CH(OR_9)_2$;

$R_9$ is selected from the group consisting of acyl having from 1 to 12 carbon atoms, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms;

$R_{10}$ is selected from the group consisting of loweralkyl, loweralkenyl, and loweralkynyl;

and wherein said compound of Formula (I) is ethylenically unsaturated at a set of locations selected from the group consisting of (a) between $C_4$ and $C_5$; (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and between $C_7$ and $C_8$;

or a pharmaceutically acceptable salt, in an amount effective to treat acne or oily skin.

8. A method of treating acne or oily skin in a subject in need thereof comprising administering to said subject, a compound of Formula (I)

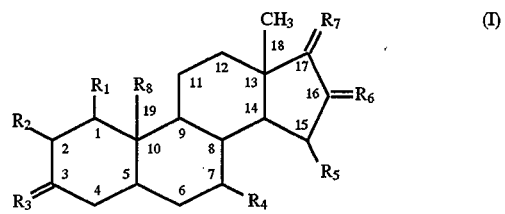

wherein:

$R_1$ is selected from the group consisting of H and α-loweralkyl;

$R_2$ is selected from the group consisting of H and β-OH;

$R_3$ is H.β-OR$_9$;

$R_4$ is selected from the group consisting of H and α-loweralkyl;

$R_5$ is selected from the group consisting of H and β-OH;

$R_6$ and $R_7$ are each independently selected from the group consisting of $H_2$, O, H.OH, H.OR$_9$, and $R_{10}$.OH;

$R_8$ is selected from the group consisting of CHO, $CH_2OH$, $CH(OH)_2$, $CH_2OR_9$ and $CH(OR_{92}$;

$R_9$ is selected from the group consisting of acyl having from 1 to 12 carbon atoms, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms;

$R_{10}$ is selected from the group consisting of loweralkyl, loweralkenyl, and loweralkynyl;

and wherein said compound of Formula (I) is ethylenically unsaturated at a set of locations selected from the group consisting of (a) between $C_4$ and $C_5$; (b) both between $C_3$ and $C_4$ and between $C_5$ and $C_6$; (c) between $C_5$ and $C_6$; (d) both between $C_4$ and $C_5$ and between $C_6$ and $C_7$; (e) both between $C_3$ and $C_4$ between $C_5$ and $C_6$ and between $C_7$ and $C_8$; (f) both between $C_4$ and $C_5$ and between $C_7$ and $C_8$; and (g) both between $C_5$ and $C_6$ and between $C_7$ and $C_8$;

or a pharmaceutically acceptable salt, in an amount effective to treat acne or oily skin.

9. A method of treating acne or oily skin in a subject in need thereof comprising administering to said subject, 19-hydroxydehydroepiandrosterone in an amount effective to treat acne or oily skin.

* * * * *

UNITED STATES PATENT AND TRADEMARK OFFICE
CERTIFICATE OF CORRECTION

PATENT NO.  : 5,661,141
DATED       : August 26, 1997
INVENTOR(S) : Petrow

It is certified that error appears in the above-identified patent and that said Letters Patent is hereby corrected as shown below:

Column 2, line 35, delete "$C_4$" second occurrence.

Column 3, line 7, "(D" should be -- (I) --.

Column 5, line 51, after "is" second occurence delete "a".

Column 6, line 13, "valetic" should be -- valeric --.

Column 12, line 35, "H.$\beta$OH" should be -- H.$\beta$-OH --.

Column 13, line 23, "$R_5$" should be -- $R_8$ --.

Column 13, line 36, "mount" should be -- amount --.

Column 16, line 48, "(MeO)3CH" should be -- $(MeO)_3CH$ --.

UNITED STATES PATENT AND TRADEMARK OFFICE
CERTIFICATE OF CORRECTION

PATENT NO. : 5,661,141
DATED : August 26, 1997
INVENTOR(S) : Petrow

It is certified that error appears in the above-identified patent and that said Letters Patent is hereby corrected as shown below:

Column 16, line 66, "AC$_2$O" should be -- Ac$_2$O --.

Column 17, line 36, "3-oxo-19-acetoxy-17/3-OH-4-" should be -- 3-oxo-19-acetoxy-17$\beta$-OH-4- --.

Column 22, line 24, "CH(OR$_{92}$" should be -- CH(OR$_9$)$_2$ --.

Signed and Sealed this

Sixteenth Day of December, 1997

Attest:

BRUCE LEHMAN

Attesting Officer

Commissioner of Patents and Trademarks